US009905415B2

(12) United States Patent
Chandra et al.

(10) Patent No.: US 9,905,415 B2
(45) Date of Patent: Feb. 27, 2018

(54) METHODS FOR DEPOSITING SILICON NITRIDE FILMS (71) Applicant: AIR PRODUCTS AND CHEMICALS, INC., Allentown, PA (US)

(72) Inventors: Haripin Chandra, San Marcos, CA (US); Anupama Mallikarjunan, San Marcos, CA (US); Xinjian Lei, Vista, CA (US); Moo-Sung Kim, Gyunggi-Do (KR); Kirk Scott Cuthill, Vista, CA (US); Mark Leonard O'Neill, Gilbert, AZ (US)

(73) Assignee: VERSUM MATERIALS US, LLC, Tempe, AZ (US)

( * ) Notice: Subject to any disclaimer, the term of this patent is extended or adjusted under 35 U.S.C. 154(b) by 0 days.

(21) Appl. No.: 14/498,044

(22) Filed: Sep. 26, 2014

(65) Prior Publication Data
US 2015/0099375 A1 Apr. 9, 2015

Related U.S. Application Data (60) Provisional application No. 61/886,406, filed on Mar. 3, 2013.

(51) Int. Cl.
C23C 16/34 (2006.01)
H01L 21/02 (2006.01)
C07F 7/10 (2006.01)
C23C 16/18 (2006.01)
C23C 16/455 (2006.01)
C23C 14/02 (2006.01)
C23C 14/54 (2006.01)
C23C 28/00 (2006.01)

(52) U.S. Cl.
CPC ............ H01L 21/0217 (2013.01); C07F 7/10 (2013.01); C23C 14/027 (2013.01); C23C 14/548 (2013.01); C23C 16/18 (2013.01); C23C 16/345 (2013.01); C23C 16/45523 (2013.01); C23C 16/45542 (2013.01); C23C 16/45553 (2013.01); C23C 28/42 (2013.01); H01L 21/0228 (2013.01); H01L 21/02211 (2013.01); H01L 21/02222 (2013.01); H01L 21/02274 (2013.01)

(58) Field of Classification Search
CPC ............ C23C 16/345; C23C 16/45525; C23C 16/45536; C23C 16/34
See application file for complete search history.

(56) References Cited

U.S. PATENT DOCUMENTS

| 5,803,975 | A | * | 9/1998 | Suzuki | C23C 16/345 |
| | | | | | 118/723 MA |
| 6,391,803 | B1 | | 5/2002 | Kim et al. | |
| 6,528,430 | B2 | | 3/2003 | Kwan et al. | |
| 7,875,312 | B2 | * | 1/2011 | Thridandam | C23C 16/402 |
| | | | | | 427/248.1 |
| 2007/0275166 | A1 | * | 11/2007 | Thridandam | C23C 16/402 |
| | | | | | 427/248.1 |
| 2008/0145535 | A1 | * | 6/2008 | Lei | C23C 16/45553 |
| | | | | | 427/255.18 |
| 2008/0145988 | A1 | * | 6/2008 | Jeon | H01L 21/28052 |
| | | | | | 438/294 |
| 2009/0075490 | A1 | | 3/2009 | Dussarrat | |
| 2009/0155606 | A1 | | 6/2009 | Yoon et al. | |
| 2010/0081293 | A1 | | 4/2010 | Mallick et al. | |
| 2011/0262642 | A1 | * | 10/2011 | Xiao | C07F 7/025 |
| | | | | | 427/255.394 |
| 2012/0128897 | A1 | * | 5/2012 | Xiao | C07F 7/025 |
| | | | | | 427/579 |
| 2012/0196048 | A1 | | 8/2012 | Ueda | |
| 2013/0183835 | A1 | | 7/2013 | Nguyen et al. | |
| 2013/0319290 | A1 | * | 12/2013 | Xiao | H01L 21/02211 |
| | | | | | 106/287.11 |
| 2013/0323435 | A1 | * | 12/2013 | Xiao | C09D 1/00 |
| | | | | | 427/579 |

(Continued)

FOREIGN PATENT DOCUMENTS

| EP | 2574611 | 4/2013 |
| JP | 2003297814 | 10/2003 |
| JP | 2010530127 A | 9/2010 |
| JP | 2012025733 A | 2/2012 |
| JP | 2012049394 A | 3/2012 |
| WO | 2005045899 | 5/2005 |
| WO | 2009039251 | 3/2009 |
| WO | 2010039363 | 4/2010 |
| WO | 2012167060 | 6/2012 |

OTHER PUBLICATIONS

Gumpher, John, et al., "Characterization of Low-Temperature Silicon Nitride LPCVD from Bis(tertiary-butylamino)silane and Ammonia". Journal of the Electrochemical Society, 151 (5) G353-G359 (2004).*

Crabtree, Kyle N., et al., "Detection of Two Highly Stable Silicon Nitrides: HSiNSi and H3SiNSi". The Journal of Physical Chemistry A, 2013, 117, 11282-11288.*

Huang, Liang, et al., "First-Principles Study of a Full Cycle of Atomic Layer Deposition of SiO2 Thin Films with Di(sec-butylamino)silane and Ozone". The Journal of Physical Chemistry C, 2013, 117, 19454-19463.*

Korman, Christopher E., et al., "Nanospore-Spanning Lipid Bilayers on Silicon Nitride Membranes That Seal and Selectively Transport Ions". Langmuir, 2013, 29, 4421-4425.*

Grow, J.M., et al., "Plasma Enhanced Chemical Vapor Deposition of Silicon Nitride from Novel Organosilanes". Mat. Res. Soc. Symp. Proc. vol. 344, 1994, pp. 241-246.*

(Continued)

Primary Examiner — Bret P Chen
(74) Attorney, Agent, or Firm — Rosaleen P. Morris-Oskanian; Michael K. Boyer; Joseph D. Rossi (57) ABSTRACT

Methods for forming silicon nitride films are disclosed that comprise the steps of: providing a substrate in a reactor; introducing into the reactor an at least one organoaminosilane having a least one $SiH_3$ group described herein wherein the at least one organoaminosilane reacts on at least a portion of the surface of the substrate to provide a chemisorbed layer; purging the reactor with a purge gas; introducing a plasma comprising nitrogen and an inert gas into the reactor to react with at least a portion of the chemisorbed layer and provide at least one reactive site wherein the plasma is generated at a power density ranging from about 0.01 to about 1.5 $W/cm^2$.

15 Claims, 3 Drawing Sheets

(56) References Cited

U.S. PATENT DOCUMENTS

2014/0273527 A1* 9/2014 Niskanen .............. C23C 16/345
438/792
2015/0147871 A1* 5/2015 Xiao ................. H01L 21/02126
438/482

OTHER PUBLICATIONS

S. Yokoyama, et al, "Atomic layer controlled deposition of silicon nitride and in situ growth observation by infrared reflection absorption spectroscopy", Applied Surface Science, 1997, 75-81.
J.W. Klaus, et al, "Atomic layer controlled growth of Si3N4 films using sequential surface reactions", Surface Science, 1998, L14-L19.
H.C.M. Knoops, et al, "Plasma-assisted ALD of Silicon Nitride from BTBAS: Influence of Plasma Exposure and Substrate Temperature", 12th International Conference on Atomic Layer Deposition, San Diego, CA.
D.H. Triyoso, et al, "Robust PEALD SiN spacer for gate first high-k metal gate integration", IEEE, 2012.
Q. Fang, et al, "Remote Plasma ALD Growth of SiO2 and SiNx Films Using Four Aminosilane Precursors", 13th International Conference on Atomic Layer Deposition, Dresden, Germany, Jun. 17-20, 2012.
H. Schuh, et al, "Disilanyl-amines—Compounds Comprising the Structural Unit Si—Si—N, as Single-Source Precursors for Plasma-Enhanced Chemical Vapour Deposition (PE-CVD) of Silicon Nitride", Z. anorg. allg. Chem., 1993, 1347-1352.

* cited by examiner

METHODS FOR DEPOSITING SILICON NITRIDE FILMS

CROSS REFERENCE TO RELATED APPLICATIONS

This application claims the benefit of U.S. Provisional Application No. 61/886,406, filed Oct. 3, 2013, which is hereby incorporated by reference as if fully set forth.

BACKGROUND OF THE INVENTION

Described herein is a method for depositing conformal, stoichiometric or non-stoichiometric, silicon nitride film using one or more organoaminosilane precursors. More specifically, described herein are plasma-based processes including, but not limited to, plasma enhanced atomic layer deposition ("PEALD"), plasma enhanced cyclic chemical vapor deposition ("PECCVD") that are used for depositing silicon nitride films that are in the fabrication of integrated circuit devices.

Low pressure chemical vapor deposition (LPCVD) processes are one of the more widely accepted methods used by semiconductor industry for the deposition of silicon nitride films. Low pressure chemical vapor deposition (LPCVD) using ammonia may require deposition temperatures of greater than 650° C. to obtain reasonable growth rates and uniformities. Higher deposition temperatures are typically employed to provide improved film properties. One of the more common industry methods to grow silicon nitride is through low pressure chemical vapor deposition in a hot wall reactor at temperatures >750° C. using the precursors silane, dichlorosilane, and/or ammonia. However, there are several drawbacks using this method. For example, certain precursors, such as silane are pyrophoric. This may present problems in handling and usage. Also, films deposited from dichlorosilane may contain certain impurities, such as chlorine and ammonium chloride, which are formed as byproducts during the deposition process.

Precursors that are used in depositing silicon nitride films such as BTBAS and chlorosilanes generally deposit the films at temperatures greater than 550° C. The trend of miniaturization of semiconductor devices and low thermal budget requires process temperature lower than 400° C. and higher deposition rate. The temperature, at which the silicon films are deposited, should decrease in order to prevent ion diffusion in the lattice, particularly for those substrates comprising metallization layers and on many Group III-V and II-VI devices.

US Publ. No. 2013/183835 ("the '835 Publication") describes methods and apparatus for forming conformal silicon nitride films at low temperatures on a substrate. The methods of forming a silicon nitride layer include performing a deposition cycle including flowing a processing gas mixture into a processing chamber having a substrate therein, wherein the processing gas mixture comprises precursor gas molecules having labile silicon to nitrogen, silicon to carbon, or nitrogen to carbon bonds, activating the precursor gas at a temperature between about 20° C. to about 480° C. by preferentially breaking labile bonds to provide one or more reaction sites along a precursor gas molecule, forming a precursor material layer on the substrate, wherein the activated precursor gas molecules bond with a surface on the substrate at the one or more reaction sites, and performing a plasma treatment process on the precursor material layer to form a conformal silicon nitride layer. The '835 Publication teaches that the processing gas mixture may further include ammonia, hydrazine, helium, argon, hydrogen, nitrogen, xenon, and helium (see the '835 Publication at [0031]). The '835 further teaches that argon and helium may be less desirable to use in the process gas mixture at higher power (e.g., greater than 1 W/cm$^2$) because it may be too reactive in a plasma state and induce excessive dissociation of the precursor molecule (instead of just assisting in the breakage of labile bonds (id.).

US Publ. No. 2009/075490 ("the '490 Publication") describes a method of preparing a silicon nitride film comprising introducing a silicon wafer to a reaction chamber; introducing a silicon nitride compound to the reaction chamber; purging the reaction chamber with an inert gas; and introducing a nitrogen-containing co-reactant in gaseous form to the reaction chamber under conditions suitable for the formation of a monomolecular layer of a silicon nitride film on the silicon wafer.

US Publ. No. 2009/155606 ("the '606 Publication") describes a cyclical method of depositing a silicon nitride film on a substrate. In one embodiment a method includes supplying a chlorosilane to a reactor in which a substrate is processed; supplying a purge gas to the reactor; and providing ammonia plasma to the reactor.

U.S. Pat. No. 6,391,803 ("the '803 patent") describes an atomic layer deposition method of forming a solid thin film layer containing Si.

U.S. Pat. No. 6,528,430 ("the '430 patent") describes an ALD method for forming silicon nitride thin films employing $Si_2Cl_6$ and $NH_3$, or $Si_2Cl_6$ and activated $NH_3$ as reactants. In one embodiment of the method, the $NH_3$ reactant is generated in a remote plasma generator to form a plasma and introduced into the chamber in an Ar carrier gas stream (see '430 patent at col. 4, lines 56-62).

U. S. Publ. No. 2010/0081293 ("the '293 Publication") describes a method for depositing a silicon nitride which includes introducing a silicon precursor and a radical nitrogen precursor to a deposition chamber. The silicon precursor has a N—"Si—"H bond, N—"Si—"Si bond and/or Si—"Si—"H bond. The radical nitrogen precursor is substantially free from included oxygen. The radical nitrogen precursor is generated outside the deposition chamber. The silicon precursor and the radical nitrogen precursor interact to form the silicon nitride based dielectric layer. The '293 Publication further teaches that the use of radical inert gas precursors that can be generated outside the deposition chamber from a starting material selected from Ne, Ar, Kr, and/or Xe (see '293 Publication at [0027]-[0028] and claim 17). The radical inert precursor can be used for depositing a silicon carbon based dielectric layer or depositing a silicon nitride based dielectric layer in combination with a radical nitrogen precursor selected from N, NH, and $NH_2$ (see id. at claim 4).

U. S. Publ. No. 2012/196048 ("the '048 Publication") describes a method for forming a thin film by alternating multiple times, respectively, a process of adsorbing a precursor onto a substrate and a process of treating the adsorbed surface using a reactant gas and a plasma, wherein the reactant gas is supplied substantially uniformly over the substrate, and the plasma is pulse-time-modulated and applied in the process of supplying the reactant gas.

The reference entitled "Atomic layer controlled growth of $Si_3N_4$ films using sequential surface reactions." Klaus, et al., Surface Science 418: L14-L19 (1998) describes a method for depositing $Si_3N_4$ thin films with atomic layer control on Si(100) substrates using sequential surface chemical reactions. The $Si_3N_4$ film growth was accomplished by separating the binary reaction $3SiCl_4+4NH_3 \rightarrow Si_3N_4+12HCl$ into two half-reactions. Successive application of the SiC$_4$ and NH$_3$ half-reactions in an ABAB . . . sequence produced Si$_3$N$_4$ deposition at substrate temperatures between 500 and 900° K and SiCl$_4$ and NH$_3$ reactant pressures of 1-10 Torr.

The reference entitled "Plasma-assisted ALD of Silicon Nitride from BTBAS: Influence of Plasma Exposure and Substrate Temperature" 12th International Conference on Atomic Layer Deposition. San Diego, Calif. Knoops, et al (ALD2013) teaches deposition of Si nitride using BTBAS (bis-aminosilane) with N$_2$ plasma. The deposited film has about 5% O$_2$ and about 5% carbon.

The reference entitled "Disilanyl-amines—Compounds Comprising the Structure Unit Si—Si—N, as Single-Source Precursors for Plasma-Enhanced Chemical Vapor Deposition (PE-CVD) of Silicon Nitride", Schuh et al., Zeitschrift Für Anorganische and Allgemeine Chemie, 619 (1993), pp. 1347-52 describes potential single-source precursors for PECVD of silicon nitride films wherein the precursors have the structural unit Si—Si—N such as (Et$_2$N)$_2$HSi—SiH$_3$, (Et$_2$N)$_2$HSi—SiH(NEt$_2$)$_2$, (i-Pr)$_2$NH$_2$Si—SiH$_3$ and [(i-Pr)$_2$N]H$_2$Si—SiH$_2$[N(i-Pr)$_2$]. The precursor 1,2-bis(di-i-propylamino)disilane (BIPADS) was used for the PECVD deposition of silicon nitride films. The resulting films from the BIPADS precursor exhibited refractive indices ranging from 1.631-1.814 and had low carbon and very low oxygen contents but high (Si-bound) hydrogen contents.

Accordingly, there is a need in the art to provide a low temperature (e.g., processing temperature of 400° C. or below) method for depositing a conformal, high quality, silicon nitride film wherein the film has one or more of the following characteristics: a density of 2.4 grams per cubic centimeter (g/cc) or greater, a low wet etch rate (as measured in dilute hydrofluoric acid (HF)), and combinations thereof compared to other silicon nitride films using other deposition methods.

BRIEF SUMMARY OF THE INVENTION

Described herein are methods for forming stoichiometric or non-stoichiometric silicon nitride films onto at least a portion of a substrate.

In one aspect, there is provided a method of forming a silicon nitride film, the method comprising the steps of:
a. providing a substrate in a reactor;
b. introducing into the reactor an at least one organoaminosilane represented by the following Formulas I, II and III below:

wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, a linear or branched C$_1$ to C$_6$ fluorinated alkyl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring, and in Formula III n=1 or 2, wherein the at least one organoaminosilane reacts on at least a portion of the surface of the substrate to provide a chemisorbed layer;
c. purging the reactor with a purge gas;
d. introducing a plasma comprising nitrogen and an inert gas into the reactor to react with at least a portion of the chemisorbed layer and provide at least one reactive site wherein the plasma is generated at a power density ranging from about 0.01 to about 1.5 W/cm$^2$; and
e. optionally purge the reactor with an inert gas; and wherein the steps b through e are repeated until a desired thickness of the silicon nitride film is obtained. In certain embodiments, R$^1$ and R$^2$ are the same. In other embodiments, R$^1$ and R$^2$ are different. In the foregoing or other embodiments, R$^1$ and R$^2$ can be linked together to form a ring. In the yet further embodiments, R$^1$ and R$^2$ are not linked together to form a ring In another aspect, there is provided a method of forming a silicon nitride film via plasma enhanced atomic layer deposition process or plasma enhanced ALD-like process, the method comprising the steps of:
a. providing a substrate in a reactor;
b. introducing into the reactor at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, Di-iso-butylaminodisilane, Di-sec-butylaminodisilane, 2,6-dimethylpiperidinosilane, di-iso-propylaminodisilane, N-methylcyclohexylaminodisilane, N-ethylcyclohexylaminodisilane, Phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane wherein the at least one organoaminosilane reacts on at least a portion of the surface of the substrate to provide a chemisorbed layer;
c. purging the reactor with a purge gas comprising at least one selected from nitrogen, a noble gas, and combinations thereof;
d. introducing a nitrogen-containing plasma into the reactor to react with at least a portion of the chemisorbed layer and provide an at least one reactive site wherein the plasma is generated at a power density ranging from about 0.01 to about 1.5 W/cm$^2$; and
e. optionally purge the reactor with an inert gas; and wherein the steps b through e are repeated until a desired thickness of the silicon nitride film is obtained. In certain embodiments, R$^1$ and R$^2$ are the same. In other embodiments, R$^1$ and R$^2$ are different. In the foregoing or other embodiments, R$^1$ and R$^2$ can be linked together to form a ring. In the yet further embodiments, $R^1$ and $R^2$ are not linked together to form a ring.

In a further aspect, there is provided a method of forming a silicon nitride film, comprising from about 5 to about 50 atomic weight percent carbon, onto at least a surface of a substrate, the method comprising the steps of:

a. providing a substrate in a reactor;

b. introducing into the reactor at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, N-isopropylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, di-iso-propylaminodisilane, di-iso-butylaminodisilane, di-sec-butylaminodisilane, 2,6-dimethylpiperidinodisilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane wherein the at least one organoaminosilane reacts on at least a portion of the surface of the substrate to provide a chemisorbed layer;

c. purging the reactor with a purge gas comprising at least one selected from nitrogen, a noble gas, and combinations thereof;

d. introducing a noble gas plasma into the reactor to react with at least a portion of the chemisorbed layer and provide an at least one reactive site wherein the plasma is generated at a power density ranging from about 0.01 to about 1.5 $W/cm^2$; and e. optionally purge the reactor with an inert gas; and wherein the steps b through e are repeated until a desired thickness of the silicon nitride film is obtained.

DETAILED DESCRIPTION OF THE INVENTION

The deposition of conformal silicon nitride films at low temperature, e.g., temperatures of 400° C. or less, which meet one or more criteria to be considered a high quality film, has been a long-standing industry challenge. A silicon nitride film is considered a "high quality" film if it has one or more of the following characteristics: a density of 2.4 grams per cubic centimeter (g/cc) or greater, a low wet etch rate (as measured in dilute hydrofluoric acid (HF)), and combinations thereof compared to other silicon nitride films.

In these or other embodiments, the refractive index for the high quality silicon nitride film should be 1.9 or higher. There are several applications in semiconductor field such as advanced patterning or spacer which require high quality films. In one embodiment, described herein is an atomic layer deposition (ALD) or ALD-like method at a low temperature, or one or more deposition temperatures ranging from about 25° C. to about 400° C., using an organoaminosilane precursor having Formulae I through III described herein in a plasma process which comprises nitrogen and optionally a noble gas.

Described herein are methods for forming stoichiometric or non-stoichiometric silicon nitride films comprising silicon and nitride onto at least a portion of a substrate. In certain embodiments, the silicon nitride film further comprises carbon. In this or other embodiments, the silicon nitride film further comprises oxygen.

The silicon nitride films described herein are deposited using at least one organoaminosilanes that comprise at least one $SiH_3$ group bonded to the nitrogen atom. The at least one organoaminosilanes are represented by the following Formulas I, II and III below:

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring; and in Formula III n=1 or 2. Exemplary organoaminosilane precursors having formula I, II and III, include, but are not limited to, are the following precursors shown in Table 1.

TABLE 1

Precursors having Formula I, II III

Di-iso-propylaminosilane

TABLE 1-continued

Precursors having Formula I, II III

Di-sec-butylaminosilane

Phenylmethylaminosilane

2,6-dimethylpiperidinosilane

N-methylcyclohexylaminosilane

N-ethylcyclohexylaminosilane

2-Methylpiperidinosilane

N-silyldecahydroquinoline

TABLE 1-continued

Precursors having Formula I, II III

2,2,6,6-tetramethylpiperidinosilane

2-(N-silylmethylamino)pyridine

N-t-butyldisilazane

N-t-pentyldisilazane

N-(2-pyridyl)disilazane

N-(3-methyl-2-pyridyl)disilazane

N-(2-methylphenyl)disilazane

TABLE 1-continued

Precursors having Formula I, II III

N-(2-ethylphenyl)disilazane

N-(2,4,6-trimethylphenyl)disilazane

N-(2,6-di-iso-pripylphenyl)disilazane

Di-iso-propylaminodisilane

Di-sec-butylaminodisilane

Phenylmethylaminodisilane

TABLE 1-continued

Precursors having Formula I, II III 2-(N-disilylmethylamino)pyridine

N-phenylethyldisilane

N-iso-propylcyclohexylaminodisilane 2,6-dimethylpiperidinodisilane 1,1-(N,N'-di-tert-butylethylenediamino)disilane N-methylcyclohexylaminodisilane TABLE 1-continued Precursors having Formula I, II III N-ethylcyclohexylaminodisilane The organoaminosilane precursors having Formulae I, II, and III described herein exhibit a balance of reactivity and stability that makes them ideally suitable as PEALD or PECCVD precursors in microelectronic device manufacturing processes. With regard to reactivity, certain precursors may have boiling points that are too high to be vaporized and delivered to the reactor to be deposited as a film on a substrate. Precursors having higher relative boiling points require that the delivery container and lines need to be heated at or above the boiling point of the precursor under a given vacuum to prevent condensation or particles from forming in the container, lines, or both. With regard to stability, other precursors may form silane ($SiH_4$) or disilane ($Si_2H_6$) as they degrade. Silane is pyrophoric at room temperature or it can spontaneously combust which presents safety and handling issues. Moreover, the formation of silane or disilane and other by-products decreases the purity level of the precursor and changes as small as 1-2% in chemical purity may be considered unacceptable for reliable semiconductor manufacture. In certain embodiments, the organoaminosilane precursors having Formulae I through III described herein comprise 2% or less by weight, or 1% or less by weight, or 0.5% or less by weight of by-product (after being stored for a time period of 6 months or greater, or one year or greater which is indicative of being shelf stable. In addition to the foregoing advantages, in certain embodiments, such as for depositing a silicon nitride film using PEALD, or PECCVD deposition method, the organoaminosilane precursor described herein may be able to deposit high density materials at relatively low deposition temperatures, e.g., 400° C. or less, or 300° C. or less, 200° C. or less, 100° C. or less. In one particular embodiment, the organoaminosilane precursor, such as Formula I precursor (e.g., di-iso-propylaminosilane or di-sec-butylaminosilane), Formula II precursor (e.g., 2,6-dimethylpiperidinosilane), or Formula III precursor (e.g., di-iso-propylaminodisilane, di-sec-butylaminodisilane, or 2,6-dimethylpiperidinodisilane) can be used to deposit a silicon nitride or silicon carbonitride film via PEALD or PECCVD at a temperature as low as 200° C. or less or at ambient or room temperature (e.g., 25° C.).

In the formulae and throughout the description, the term "cyclic alkyl" denotes a cyclic functional group having from 3 to 10 or from 4 to 10 carbon atoms or from 5 to 10 carbon atoms. Exemplary cyclic alkyl groups include, but are not limited to, cyclobutyl, cyclopentyl, cyclohexyl, and cyclooctyl groups.

In the formulae and throughout the description, the term "aryl" denotes an aromatic cyclic functional group having from 5 to 12 carbon atoms or from 6 to 10 carbon atoms. Exemplary aryl groups include, but are not limited to, phenyl, benzyl, chlorobenzyl, tolyl, and o-xylyl.

In the formulae and throughout the description, the term "alkenyl group" denotes a group which has one or more carbon-carbon double bonds and has from 3 to 10 or from 3 to 6 or from 3 to 4 carbon atoms.

In the formulae and throughout the description, the term "alkynyl group" denotes a group which has one or more carbon-carbon triple bonds and has from 3 to 10 or from 3 to 6 or from 3 to 4 carbon atoms.

In the formulae and throughout the description, the term "dialkylamino group" denotes a group which has two alkyl groups attached to a nitrogen atom and has from 1 to 10 or from 2 to 6 or from 2 to 4 carbon atoms. Exemplary aryl groups include, but are not limited to dimethylamino, diethylamino, and ethylmethylamino.

The term "electron withdrawing group" as used herein describes an atom or group thereof that acts to draw electrons away from the Si—N bond. Examples of suitable electron withdrawing groups or substituents include, but are not limited to, nitriles (CN). In certain embodiments, electron withdrawing substituent can be adjacent to or proximal to N in any one of Formula I. Further non-limiting examples of an electron withdrawing group includes F, Cl, Br, I, CN, $NO_2$, RSO, and/or $RSO_2$ wherein R can be a $C_1$ to $C_{10}$ alkyl group such as, but not limited to, a methyl group or another group.

In certain embodiments, one or more of the alkyl group, alkenyl group, alkynyl group, alkoxy group, dialkylamino group, aryl group, and/or electron withdrawing group in Formulae I through III may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxy group, dialkylamino aryl group, and/or electron withdrawing group in Formulae I through III may be unsubstituted.

The method used to form the silicon nitride films or coatings are deposition processes. Examples of suitable deposition processes for the method disclosed herein include, but are not limited to, plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the silicon nitride film is deposited using an ALD process. In another embodiment, the silicon nitride film is deposited using a CCVD process. In a further embodiment, the silicon nitride film is deposited using a thermal CVD process. The term "reactor" as used herein, includes without limitation, reaction chamber or deposition chamber. The ALD-like process is defined herein as a cyclic CVD process that provides a high conformal silicon nitride film such as, silicon nitride or silicon carbonitride on a substrate as shown by having at least one of the following: percentage of non-uniformity of about 5% or less as measured by ellipsometer, a deposition rate of 1 Å or greater per cycle, or a combination thereof.

In certain embodiments, the method disclosed herein avoids pre-reaction of the precursors by using PEALD or PECCVD methods that separate the precursors prior to and/or during the introduction to the reactor. In this connection, deposition techniques such as PEALD or PECCVD processes are used to deposit the silicon nitride film. In one embodiment, the film is deposited via a PEALD process by exposing the substrate surface alternatively to the one or more the silicon nitride precursor, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon nitride precursors other than the organoaminosilane precursor having the above Formulae I through III. Examples of additional silicon nitride precursors include, but are not limited to, monochlorosilane, dichlorosilane, hexachlorodisilane.

Depending upon the deposition method, in certain embodiments, the at least one organoaminosilane precursors may be introduced into the reactor at a predetermined molar volume, or from about 0.1 to about 1000 micromoles. In this or other embodiments, the at least one organoaminosilane precursor may be introduced into the reactor for a predetermined time period. In certain embodiments, the time period ranges from about 0.001 to about 500 seconds.

In certain embodiments, the silicon nitride films comprise silicon and nitrogen. In these embodiments, the silicon nitride films deposited using the methods described herein are formed in the presence of nitrogen-containing source. A nitrogen-containing source may be introduced into the reactor in the form of at least one nitrogen-containing source and/or may be present incidentally in the other precursors used in the deposition process. Suitable nitrogen-containing source gases may include, for example, nitrogen/argon plasma. In certain embodiments, the nitrogen-containing source comprises nitrogen/argon plasma source gas that is introduced into the reactor at a flow rate ranging from about 1 to about 2000 standard cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

In the method described herein, a nitrogen-containing plasma comprising a nitrogen containing gas such as, without limitation, nitrogen and optionally a noble gas can be generated in situ or remotely, preferably a noble gas with an atomic mass greater than nitrogen's atomic mass (i.e., 28 amu). The presence of a noble gas with atomic mass greater than nitrogen's atomic mass is believed to create more atomic nitrogen radicals. The nitrogen plasma source gas is introduced into the reactor at a flow rate ranging from about 1 to about 2000 square cubic centimeters (sccm) or from about 1 to about 1000 sccm or more. The nitrogen containing plasma can be introduced for a time that ranges from about 0.01 to about 100 seconds or more. In embodiments, the precursor pulse can have a pulse duration that is greater than 0.01 seconds, and the nitrogen-containing plasma can have a pulse duration that is less than 0.01 seconds, while the water pulse duration can have a pulse duration that is less than 0.01 seconds. In yet another embodiment, the purge duration between the precursor pulse and nitrogen plasmas that can be as low as 0 seconds. In yet another embodiment, a hydrogen plasma can be generated in situ or remotely using pure hydrogen ($H_2$)) mixed with a noble gas when a hydrogen plasma can be employed. The weight percentage of the noble gas in the plasma containing both nitrogen and noble gas can vary from 1 wt % to 99% whereas the weight percentage of the noble gas in the plasma containing both hydrogen and noble gas can also vary from 1 wt % to 99%.

As demonstrated in the working examples herein, conventional nitrogen containing plasma disclosed in prior art such as ammonia plasma, hydrogen/nitrogen plasma could not provide high quality silicon nitride using existing organoaminosilanes such as BTBAS. Not being bound by theory, it is believed the plasma containing both nitrogen and a noble gas such as argon can help the formation of a silicon nitride film as well as provide reactive sites on at least a portion of the chemisorbed surface for organoaminosilanes having Formulae I through III and at least one $SiH_3$ group in subsequent deposition cycles to anchor onto these reactive sites. This enables the cyclical, deposition to occur whereas conventional nitrogen containing plasma such as ammonia plasma, hydrogen/nitrogen plasma may poison the surface, thereby resulting in minimum film deposition. Not being bound by any theory, the plasma density which is defined by plasma power over area of electrodes (for example, plasma power of 450 W for a 6" wafer ALD reactor, the plasma density is about 2.5 $W/cm^2$ assuming the area of electrode is same as the wafer) and is preferably lower than 2 $W/cm^2$ in order to reduce potential plasma damage on the substrate as well as any built-in structures on the substrate, yet still produce high quality silicon nitride film which can be implemented into semi-conductor manufacturing processes. The plasma density of the method described herein ranges from about 0.01 to about 2 $W/cm^2$, or from about 0.01 to about 1.5 $W/cm^2$, or from about 0.01 to 1 $W/cm^2$. Typical plasma frequency ranges from 10 KHz to 2.4 GHz, preferably 10 kHz to 60 MHz. In some embodiments, dual RF plasma can be employed, one low frequency ranging from 10 kHz to 1 MHz and the other middle frequency selected from group consisting of 13.56 MHz and 27.1 MHz.

The deposition methods described herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon (Ne), hydrogen ($H_2$), and mixtures thereof. In certain embodiments, the inert gas that is used as a purge gas comprises a noble gas. The term "noble gas" as used herein means those gases found in Group 18 of the Periodic Table and include, helium (He), neon (Ne), argon (Ar), Xenon (Xe), krypton (Kr), and mixtures thereof. In one particular embodiment, the noble gas used as a purge gas comprises argon. In this or other embodiments, the purge gas comprising Ar is supplied into the reactor at a flow rate ranging from about 10 to about 2000 sccm for about 0.1 to 1000 seconds, thereby purging the unreacted precursor material and any byproduct that may remain in the reactor.

The respective step of supplying the precursors, the nitrogen-containing source, and/or other precursors, source gases, and/or reagents may be performed by changing the time for supplying them to change the stoichiometric composition of the resulting silicon nitride film.

Energy is applied to the at least one of the precursor, nitrogen-containing source, reducing agent, other precursors or combination thereof to induce reaction and to form the silicon nitride film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors may be delivered to the reaction chamber such as a PEALD or PECCVD reactor either single wafer or batch in a variety of ways such as bubbling, vapor draw, or direct liquid injection (DLI). In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

In certain embodiments, the gas lines connecting from the precursor canisters to the reaction chamber are heated to one or more temperatures depending upon the process requirements and the container of the organoaminosilane precursor having the formulae I through III described herein is kept at one or more temperatures for bubbling. In other embodiments, a solution comprising the at least one silicon nitride precursor having the formula described herein is injected into a vaporizer kept at one or more temperatures for direct liquid injection.

A flow of argon and/or other inert gas may be employed as a carrier gas to help deliver the vapor of the at least one organoaminosilane precursor to the reaction chamber during the precursor pulsing. In certain embodiments, the reaction chamber process pressure is about 2 Torr or less. In other embodiments, the reaction chamber process pressure is about 10 Torr or less.

In a typical PEALD or PECCVD or PEALD-like process, a substrate such as, without limitation, a silicon oxide, carbon doped silicon oxide, flexible substrate, or metal nitride substrate is heated on a heater stage in a reaction chamber that is exposed to the silicon nitride precursor initially to allow the organoaminosilane to chemically adsorb onto the surface of the substrate. A purge gas such as nitrogen, argon, or other inert gas purges away unabsorbed excess organoaminosilane from the process chamber. After sufficient purging, an nitrogen-containing source may be introduced into reaction chamber to react with the absorbed surface followed by another gas purge to remove reaction by-products from the chamber. The process cycle can be repeated to achieve the desired film thickness. In other embodiments, pumping under vacuum can be used to remove unabsorbed excess organoaminosilane from the process chamber, after sufficient evacuation under pumping, a nitrogen-containing source may be introduced into reaction chamber to react with the absorbed surface followed by another pumping down purge to remove reaction by-products from the chamber.

In one aspect, there is provided a method of forming a silicon nitride film, the method comprising the steps of:
  a. providing a substrate in a reactor;
  b. introducing into the reactor an at least one organoaminosilane represented by the following Formulas I, II and III below:

wherein $R^1$ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; $R^2$ is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, a linear or branched $C_1$ to $C_6$ fluorinated alkyl group, an electron withdrawing group, and a $C_4$ to $C_{10}$ aryl group; optionally wherein $R^1$ and $R^2$ are linked together to form a ring selected from a substituted or unsubstituted aromatic ring or a substituted or unsubstituted aliphatic ring, and in Formula III n=1 or 2, wherein the at least one organoaminosilane reacts on at least a portion of the surface of the substrate to provide a chemisorbed layer;
  c. purging the reactor with a purge gas;
  d. introducing a plasma comprising nitrogen and an inert gas into the reactor to react with at least a portion of the chemisorbed layer and provide at least one reactive site wherein the plasma is generated at a power density ranging from about 0.01 to about 1.5 W/cm²; and
  e. optionally purge the reactor with an inert gas; and wherein the steps b through e are repeated until a desired thickness of the silicon nitride film is obtained. In certain embodiments, $R^1$ and $R^2$ are the same. In other embodiments, $R^1$ and $R^2$ are different. In the foregoing or other embodiments, $R^1$ and $R^2$ can be linked together to form a ring. In the yet further embodiments, $R^1$ and $R^2$ are not linked together to form a ring. Optionally a plasma comprising hydrogen can be inserted before step d to help removing hydrocarbon generated from the reaction between the organoaminosilane and the surface. The plasma comprising hydrogen is selected from the group consisting of hydrogen plasma, hydrogen/helium, hydrogen/argon plasma, hydrogen/neon plasma and mixtures thereof.

In another aspect, there is provided a method of forming a silicon nitride film via plasma enhanced atomic layer deposition process or plasma enhanced ALD-like process, the method comprising the steps of:

a. providing a substrate in a reactor;

b. introducing into the reactor at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, N-isopropylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, di-iso-propylaminodisilane, di-iso-butylaminodisilane, di-sec-butylaminodisilane, 2,6-dimethylpiperidinosilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane wherein the at least one organoaminosilane reacts on at least a portion of the surface of the substrate to provide a chemisorbed layer;

c. purging the reactor with a purge gas comprising at least one selected from nitrogen, a noble gas, and combinations thereof;

d. introducing a nitrogen-containing plasma into the reactor to react with at least a portion of the chemisorbed layer and provide an at least one reactive site wherein the plasma is generated at a power density ranging from about 0.01 to about 1.5 W/cm$^2$; and e. optionally purge the reactor with an inert gas; and wherein the steps b through e are repeated until a desired thickness of the silicon nitride film is obtained.

The above steps define one cycle for the method described herein; and the cycle can be repeated until the desired thickness of a silicon nitride film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen-containing source may be performed by varying the duration of the time for supplying them to change the stoichiometric composition of the resulting silicon nitride film, although always using nitrogen in less than a stoichiometric amount relative to the available silicon.

In certain embodiments of the method described herein, steps b to e are repeated to provide a silicon nitride film with a thickness ranging from about 0.1 to about 500 Å, or from about 0.1 to about 5 Å, or from about 0.1 to about 10 Å, or about 0.1 to about 50 Å, or 0.1 to 100 Å. In one particular embodiment of the method described herein, a plasma comprising hydrogen can be inserted before step d to help removing hydrocarbon generated from the reaction between the organoaminosilane and the surface. The plasma comprising hydrogen is selected from the group consisting of hydrogen plasma, hydrogen/helium, hydrogen/argon plasma, hydrogen/neon plasma and mixtures thereof.

In certain embodiments, the resultant silicon nitride containing films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the silicon nitride containing films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. An example of the silicon containing or silicon nitride film that is formed using the organoaminosilane precursors and processes described herein has the formulation $Si_xO_yC_zN_vH_w$, wherein Si ranges from about 10% to about 40%; O ranges from about 0% to about 5%; C ranges from about 0% to about 10%; N ranges from about 0% to about 75% or from about 0% to 50%; and H ranges from about 0% to about 10% atomic percent weight % wherein x+y+z+v+w=100 atomic weight percent, as determined for example, by XPS or other means.

In one particular embodiment wherein the film is depositing using a plasma comprising a noble gas, the silicon nitride film comprises from about 5% to about 50% carbon atomic weight percent, as determined for example, by XPS or other means. In this particular embodiment, the silicon nitride film further comprises wherein Si ranges from about 10% to about 40%; O ranges from about 0% to about 5%; N ranges from about 0% to about 75% or from about 0% to 50%; and H ranges from about 0% to about 10% atomic percent weight % wherein the total weight percent of the film adds up to 100 atomic weight percent.

As mentioned previously, the method described herein may be used to deposit a silicon nitride film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, a flexible substrate such as IGZO, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nanoelectromechanical systems, thin film transistor (TFT), light emitting diodes (LED), organic light emitting diodes (OLED), IGZO, and liquid crystal displays (LCD).

The following examples illustrate the method for depositing silicon nitride films described herein and are not intended to limit it in any way.

EXAMPLES

In the following examples, unless stated otherwise, properties were obtained from sample films that were deposited onto medium resistivity (14-17 Ω-cm) single crystal silicon wafer substrates. All film depositions were performed using either the 300 mm production tool, the ASM Stellar 3000 PEALD reactor, or the CN-1, a 150 mm laboratory scale showerhead type ALD reactor.

The ASM Stellar reactor tool is a single wafer production tool. The reactor chamber was Folded Lateral Reactor (FLR) equipped with a 27.1 MHz direct plasma. In typical depositions, unless stated otherwise, the chamber pressure was fixed at 2 Torr. Additional inert gas was used during the depositions to maintain chamber pressure. The organoaminosilane precursor was delivered to the reactor chamber using either vapor draw at 15 Torr or accompanied by 200 standard cubic centimeters (sccm) of Ar gas at 1 Torr vapor pressure. All of the examples, including the comparative examples, were conducted using a RF Plasma power of 500 W over electrode area of about that of 300 mm wafer which provided a power density of 0.7 W/cm$^2$ The CN-1 reactor has showerhead design with 13.56 MHz direct plasma. In typical process conditions, unless stated otherwise, the chamber pressure was fixed to 2 Torr. Additional inert gas was used to maintain chamber pressure. The organoaminosilane precursor was delivered using 50 sccm of Ar at 14 Torr vapor pressure or, in the case of a nitrogen-only process precursor was delivered using vapor draw (i.e. no argon used at all). Typical RF power used was 125 W over electrode area of 150 mm wafer to provide a power density of 0.7 W/cm$^2$. The film depositions comprised the steps listed in Table 2. Steps 1 through 4 in Table 2 constitute one PEALD cycle and were repeated and unless otherwise specified repeated a total of 1000 times to get the desired film thickness.

TABLE 2

Steps used in PEALD silicon nitride containing films

| Step | |
|---|---|
| 1 | Introduce an organoaminosilane precursor to the reactor; additional inert gas is used to maintain chamber pressure to provide a chemisorbed layer |
| 2 | Purge the organoaminosilane precursor from the reactor chamber with inert gas |
| 3 | Activate a plasma to react with the surface of the chemisorbed layer and create reactive sites |
| 4 | Purge unreacted plasma species out |

The reactive index (RI) and thickness for the deposited films were measured using an ellipsometer. Film non-uniformity was calculated using the standard equation: % non uniformity=((max thickness−min thickness)/(2*average (avg) thickness)). Film structure and composition were analyzed using Fourier Transform Infrared (FTIR) spectroscopy and X-Ray Photoelectron Spectroscopy (XPS). The density for the films was measured with X-ray Reflectometry (XRR). Wet etch rate were performed in a dilute HF solution, 49% HF water ratio of 1:99. A thermal oxide SiO$_2$ film was etched with the same schedule to verify solution concentration consistency.

Comparative Example 1. PEALD Silicon Nitride Film Using Bis(Tert-Butylamino)Silane (BTBAS) and Ar/N$_2$ Plasma The silicon wafer was loaded into Stellar 3000 PEALD reactor and heated to a temperature of 300° C. with a chamber pressure of about 2 Torr. The deposition process was as described in Table 2, repeated 1000 times, under the following process conditions:

1. Deliver an organoaminosilane precursor: bis(tert-butylamino)silane (BTBAS)
   Delivery method: vapor draw
   Argon flow: 300 sccm
   BTBAS pulse: 1 second
2. Inert gas purge
   Argon flow: 300 sccm
   Purge time: 2 seconds
3. Plasma on
   Argon flow: 300 sccm
   Nitrogen flow: 400 sccm
   Plasma power: 500 W (0.7 W/cm$^2$)
   Plasma time: 5 seconds
4. Purge plasma
   Argon flow: 300 sccm
   Purge time: 2 seconds A silicon nitride film was deposited at 0.41 Å/cycle with refractive index of 1.84. Film contained 1.3% oxygen and 11.7% carbon with density of 2.3 g/cc. Film wet etch rate is higher than 4.5 Å/sec (27 nm/min).

Comparative Example 2. PEALD Silicon Nitride Film Using Bis(Diethylamino)Silane (BDEAS) and Ar/N$_2$ Plasma The silicon wafer was loaded into Stellar 3000 PEALD reactor and heated to a temperature of 300° C. with a chamber pressure of about 2 Torr. The deposition process was the same as described in Comparative Example 1.

A silicon nitride film was deposited at 0.22 Å/cycle with refractive index of 1.88. Film contained 3.9% oxygen, 11.9% carbon with density of 2.2 g/cc. Film wet etch rate is higher than 3.75 Å/sec (>23 nm/min).

Comparative Example 3. PEALD Silicon Nitride Film Using Bis(Tert-Butylamino)Silane (BTBAS) and Ar/NH$_3$ Plasma The silicon wafer was loaded into Stellar 3000 PEALD reactor and heated to 300° C. with a chamber pressure of about 2 Torr. The deposition process was conducted as described in Table 2, repeated 1000 times, under the following process conditions:

1. Deliver an organoaminosilane precursor: bis(tert-butylamino)silane (BTBAS)
   Delivery method: vapor draw
   Argon flow: 300 sccm
   BTBAS pulse: 1 second
2. Inert gas purge
   Argon flow: 300 sccm
   Purge time: 2 seconds
3. Plasma on
   Argon flow: 300 sccm
   Ammonia flow: 400 sccm
   Plasma power: 500 W (0.7 W/cm$^2$)
   Plasma time: 5 seconds
4. Purge plasma
   Argon flow: 300 sccm
   Purge time: 2 seconds Silicon nitride film with minimum deposition rate (<0.05 Å/cycle) observed. Film is too thin to measure refractive index accurately.

Example 1. PEALD Silicon Nitride Film Using Di-Iso-Propylaminosilane (DIPAS) and Ar/N$_2$ Plasma The silicon wafer was loaded into Stellar 3000 PEALD reactor and heated to 300° C. with chamber pressure of about 2 Torr. The deposition process was performed using the steps described in Table 2 and repeated 1000 times. Process conditions used was the same as described in Comparative Example 1, with varying precursor pulse: 0.5 to 5 seconds. The deposition rates and refractive index are summarized in Table 3 below.

TABLE 3

Deposition rate and refractive index of deposited films for silicon nitride containing films using DIPAS and Ar/N$_2$ plasma

| Sample No. | DIPAS pulse (s) | Deposition Rate (Å/cycle) | Refractive index |
|---|---|---|---|
| 1 | 0.5 | 0.18 | 1.97 |
| 2 | 1 | 0.20 | 1.96 |
| 3 | 1 | 0.20 | 1.95 |
| 4 | 2 | 0.24 | 1.95 |
| 5 | 5 | 0.30 | 1.94 |
| 6 | 5 | 0.25 | 1.95 |

TABLE 4

Properties of silicon nitride film using DIPAS and Ar/N$_2$ plasma

| Sample No. | C (%) | O content (%) | Density (g/cc) | WER in dHF (Å/sec) |
|---|---|---|---|---|
| 2 | 5.6 | 2.8 | 2.8 | 0.4 |
| 5 | 5.2 | 1.5 | 2.7 | 0.3 |
| 6 | 6.2 | 2.1 | 2.7 | 0.4 |

Films 2, 5 and 6 were picked to represent the examples for further film characterizations. Film impurities, density and wet etch rate in dilute HF for these films were measured and the results are provided below in Table 4. As the results in Table 4 indicate, Silicon nitride films deposited from DIPAS had a lower carbon content, higher density, and a lower wet etch rate than the BTBAS deposited films in Comparative Example 1.

Example 2. PEALD Silicon Nitride Containing Film Using Di-Sec-Butylaminosilane (DSBAS) and Ar/N$_2$ Plasma The deposition process was performed using the steps described in Table 2 and repeated 1000 times. The process conditions used were the same as described in Comparative Example 1, with a varying precursor pulse ranging from 0.2 to 5 seconds. The deposition rate and refractive index for all deposited films were measured and are provided below in Table 5. Both deposition rate and refractive index shows are consistent with DIPAS as shown in Example 1.

TABLE 5

Deposition rate and refractive index of deposited films for silicon nitride containing films using DSBAS and Ar/N$_2$ plasma

| Sample No. | DSBAS pulse (s) | Deposition Rate (Å/cycle) | Refractive index |
|---|---|---|---|
| 1 | 0.2 | 0.16 | 1.96 |
| 2 | 0.5 | 0.19 | 1.93 |
| 3 | 1 | 0.22 | 1.92 |
| 4 | 5 | 0.30 | 1.90 |

Example 3. PEALD Silicon Nitride Containing Film Using Di-Sec-Butylaminosilane (DSBAS) and Ar/N$_2$ Plasma with Various Percentages of Argon (Ar)

The silicon wafer was loaded into Stellar 3000 PEALD reactor and heated to 300° C. with chamber pressure of about 2 Torr. DSBAS was delivered to the chamber at 1 Torr vapor pressure using 200 sccm Ar carrier gas at room temperature. Substrate temperature was set to 300° C. Gas and precursor lines temperature were adjusted accordingly to prevent condensation prior to the reactor. The deposition was conducted using the steps described in Table 2 and using the following process parameters:

1. Introduce an organoaminosilane precursor to the reactor: DSBAS

Argon flow=300 sccm

Si precursor pulse: 1 second

2. Inert gas purge

Argon flow: 300 sccm

Purge time: 5 seconds

3. Plasma on

Argon flow: 325 to 425 sccm

Nitrogen flow: 75 to 200 sccm

Total flow of Ar and nitrogen: 500 sccm

Chamber pressure: 2 Torr

Plasma power: 500 W (0.7 W/cm$^2$)

Plasma time: 5 seconds

4. Purge plasma

Argon flow: 300 sccm

Chamber pressure: 2 Torr

Purge time: 0.5 second

Growth per cycle (GPC) and refractive index for silicon nitride films deposited with DSBAS and Ar/N$_2$ plasma using various ratios of Ar vs. N$_2$ was calculated and are provided in Table 6.

TABLE 6

GPC and refractive index of film deposited from di-sec-butylaminosilane (DSBAS)

| Sample ID | Ar flow (sccm) | N$_2$ flow (sccm) | Ar/total flow | GPC (Å/cycle) | % non-uniformity | Ref. Index |
|---|---|---|---|---|---|---|
| 1-1 | 300 | 200 | 60% | 0.17 | 14.4% | 1.994 |
| 1-2 | 375 | 125 | 75% | 0.25 | 4.3% | 1.977 |
| 1-3 | 425 | 75 | 85% | 0.24 | 6.1% | 1.935 |

Table 7 contains carbon content, measured by XPS, and dilute HF wet etch rate comparison for silicon nitride containing films deposited from di-sec-butylaminosilane (DSBAS) and Ar/N$_2$ plasma with various ratio of argon to nitrogen. Optimizing argon and nitrogen flow improves growth per cycle (GPC) and film uniformity without affecting film properties. In either case, the deposited films carbon content was 6-7%, the etch rate was 0.50 Å/s and the film density was 2.8 g/cc.

TABLE 7

Films properties from di-sec-butylaminosilane (DSBAS)

| Sample ID | Ar flow (sccm) | N₂ flow (sccm) | Ar/total flow | C content (%) | dHF wet etch rate (Å/sec) | Density (g/cc) |
|---|---|---|---|---|---|---|
| 1-1 | 300 | 200 | 60% | 6.8% | 0.50 | 2.8 |
| 1-2 | 375 | 125 | 75% | 6.1% | 0.55 | 2.8 |

Example 4: PEALD Silicon Nitride Containing Silicon Nitride Film Using Phenylmethylaminosilane (PMAS) and Ar/N$_2$ Plasma The silicon wafer was loaded into Stellar 3000 PEALD reactor and heated to 300° C. with chamber pressure of about 2 Torr. PMAS was delivered to the chamber at 1 Torr vapor pressure using 200 sccm Ar carrier gas at room temperature. Substrate temperature was set to 300° C. Gas and precursor lines temperature were adjusted accordingly to prevent condensation prior to the reactor. The deposition was conducted using the steps described in Table 2 under process parameters similar to those provided in Example 3. During the plasma step or step 3, the argon and nitrogen flow were 300 sccm and 200 sccm respectively. The resulting film had a growth per cycle of 0.18 Å/cycle and refractive index of 1.95. The film also had a dilute HF WER of 0.53 Å/sec.

Example 5: PEALD Silicon Nitrogen Containing Film Using Phenylmethylaminodisilane (PMADS) and Ar/N$_2$ Plasma The silicon wafer was loaded into Stellar 3000 PEALD reactor and heated to 300° C. with chamber pressure of about 2 Torr. PMADS was delivered to the chamber at 1 Torr vapor pressure using 200 sccm Ar carrier gas at room temperature. Substrate temperature was set to 300° C. Gas and precursor lines temperature were adjusted accordingly to prevent condensation prior to the reactor. The deposition was conducted using the steps described in Table 2 and the process parameters provided in Example 3. During the plasma step or step 3, the argon and nitrogen flow were 300 sccm and 200 sccm, respectively. The resulting film had growth per cycle of 0.22 Å/cycle and a refractive index of 1.94. The film also had a dilute HF WER of 0.77 Å/s and carbon impurities of 7.0% atomic weight % (at. %).

Example 6: PEALD Silicon Nitride Containing Silicon Nitride Containing Film Using Di-Iso-Propylaminodisilane (DIPADS) and Ar/N$_2$ Plasma The silicon wafer was loaded into Stellar 3000 PEALD reactor and heated to 300° C. with a chamber pressure of about 2 Torr. DIPADS was delivered to the chamber at 15 Torr using vapor draw. The substrate temperature was set to 300° C. Gas and precursor lines temperature were adjusted accordingly to prevent condensation prior to reaching the reactor. The deposition was conducted using the steps described in Table 2 and using the process parameters provided in Example 3. During plasma step or step 3, the argon and nitrogen flow were 300 sccm and 200 sccm, respectively. The resulting film had a growth per cycle of 0.26 Å/cycle and a refractive index of 1.92. The film also has a dilute HF WER of 0.67 Å/s and carbon impurities of 4.9 at. %.

Example 7. Comparison of the Electrical Properties of PEALD Films Deposited Using Di-Sec-Butylaminosilane (DSBAS) and Bis(t-Butylamino)Silane (BTBAS) Electrical Properties Films were deposited using a monoaminosilane precursor or di-sec-butylaminosilane (DSBAS) and the following bis-aminosilane precursors or bis(t-butylamino)silane (BTBAS) and bis(diethylamino)silane (BDEAS) in the ASM Stellar PEALD tool. The precursors were delivered to the chamber at 1 Torr vapor pressure using 200 sccm Ar carrier gas at room temperature. The substrate temperature was set to 300° C. The deposition was conducted using the process steps provided in Table 2 and using the process condition described in Example 3, and using 375 sccm of Ar and 125 sccm of N$_2$ during plasma step or step 3.

Figure 1:
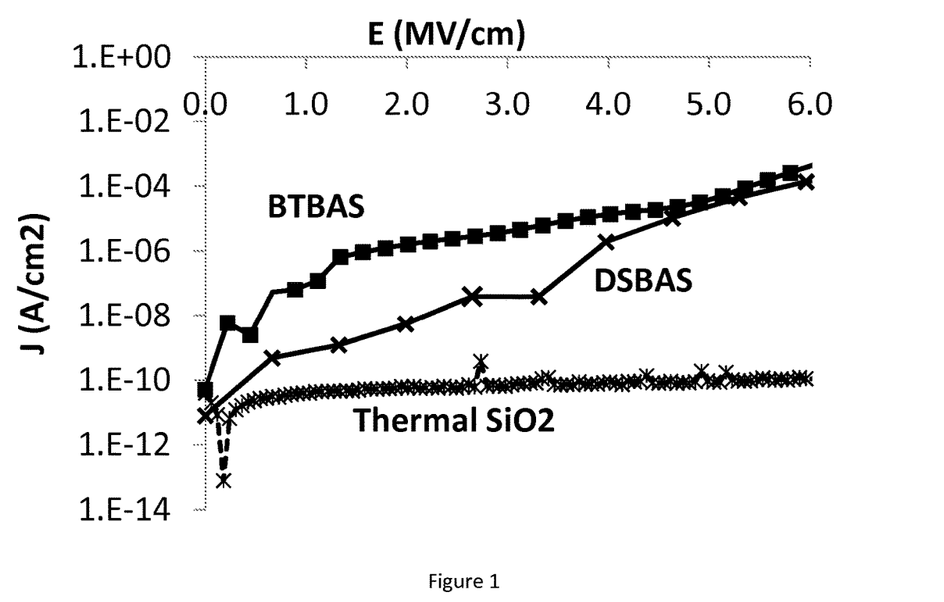
FIG. 1 provides a leakage breakdown comparison of silicon nitride films deposited from bis(tert-butylamino)silane (BTBAS) and di-sec-butyl-aminosilane (DSBAS) which were deposited at a temperature of 300° C.

The leakage current comparison of the deposited films from DSBAS and BTBAS is shown in FIG. 1. FIG. 1 shows that the DSBAS deposited films had a higher than one order of magnitude better leakage current (J) at a low electrical field (E) (<4 MV/cm).

Examples 8. Comparison of PEALD Films Deposited Using Di-Sec-Butylaminosilane (DSBAS) and Bis(t-Butylamino)Silane (BTBAS) and Bis(Diethylamino)Silane (BDEAS)

Films were deposited using the precursors di-sec-butylaminosilane (DSBAS) and bis(t-butylamino)silane (BTBAS) and bis(diethylamino)silane (BDEAS) in the ASM Stellar 3000 PEALD tool. The precursors were each delivered to the chamber at 1 Torr vapor pressure using 200 sccm Ar carrier gas at room temperature. The substrate temperature was set to 200° C. The gas and precursor lines temperature were adjusted accordingly to prevent condensation prior to the reactor. Other than the foregoing, the deposition was conducted as described in Example 7. The refractive index and growth per cycle for each deposited film was measured immediately after deposition and provided Table 8.

TABLE 8

Comparison of As-Deposited Films Deposited from DSBAS, BTBAS, and BDEAS at 200° C.

| Precursor | GPC (Å/cycle) | Refractive index |
|---|---|---|
| DSBAS | 0.33 | 1.86 |
| BTBAS | 0.87 | 1.75 |
| BDEAS | 0.71 | 1.54 |

Figure 2:
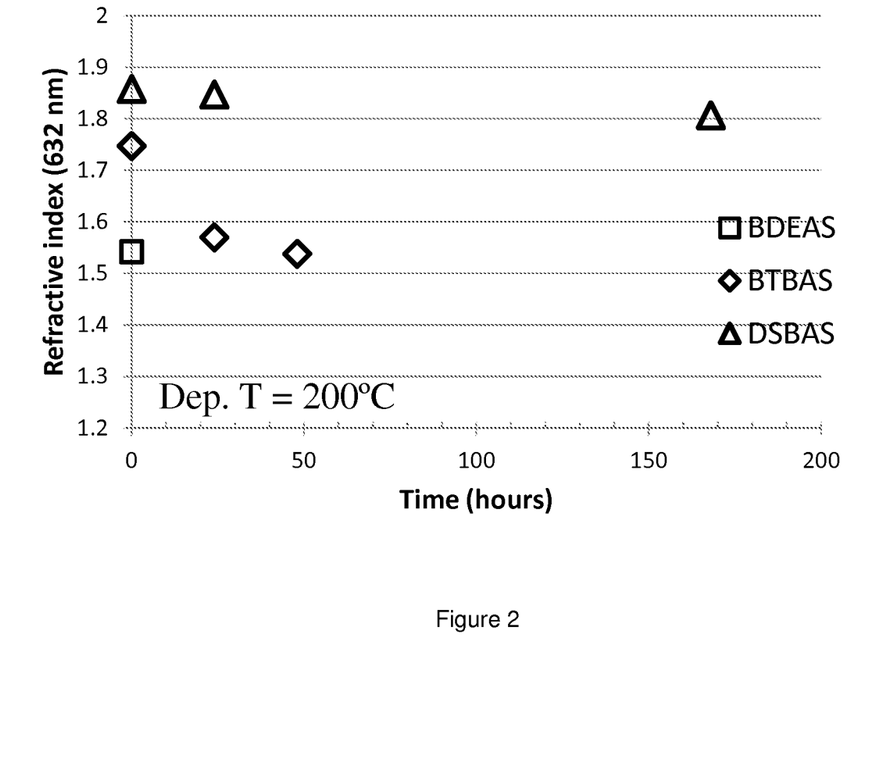
FIG. 2 provides a refractive index stability comparison of silicon nitride films deposited from the following precursors: DSBAS, BTBAS, and bis(diethylamino)silane (BDEAS).
Figure 3:
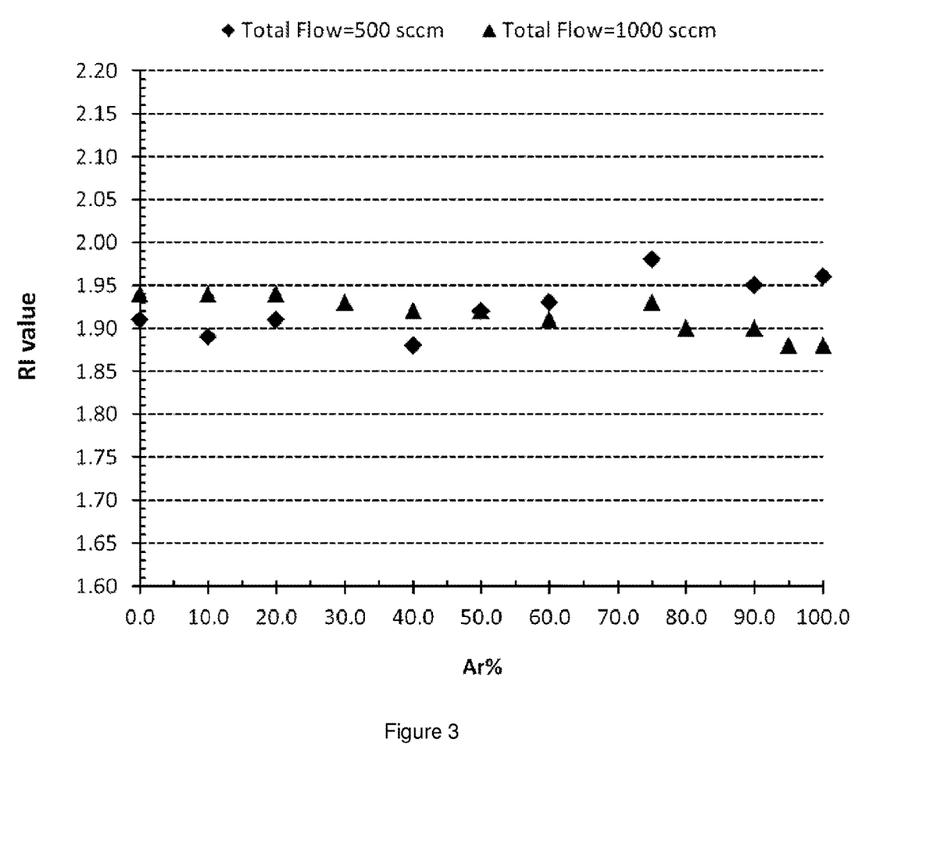
FIG. 3 provides the relationship between refractive index (RI) versus argon (Ar) percentage of total flow using di-iso-propylaminosilane (DIPAS).

Referring to Table 8, from the films deposited using the monoaminosilane precursor DSBAS had the highest refractive index, indicating it is more a silicon nitride films. Of the bisaminosilanes, BDEAS had the lowest refractive index, 1.54, indicating more silicon oxide like films. The refractive index of these films was re-measured after the samples were stored in an ambient atmosphere. FIG. 2 shows that the refractive index of the films decreased over time due to oxidation. Of the three films, the monoaminosilane-deposited film DSBAS film had higher stability than either of the bisaminosilane deposited films or BTBAS or BDEAS. Of the bisaminosilane-deposited films, BTBAS film showed a refractive index decrease from 1.75 to 1.57 after approximately one day (~24 hours) in ambient. The remaining bisaminosilane-deposited film or BDEAS exhibited even worse stability or a film refractive index is 1.57 right after deposition. The films were analyzed for composition via XPS after sitting in ambient for 150 hours (7 days). The XPS analysis showed that both bis(amino)silane-deposited films or the BDEAS and BTBAS deposited films contained 58% O, 6% C and 3.5% N whereas the monoaminosilane-deposited films or DSBAS film contained 2.5% O, 13.9% C, and 41% N. Thus, the DSBAS deposited film was more stable than either the BTBAS or BDEAS deposited film.

Example 9. PEALD Silicon Nitride Containing Film Using Di-Iso-Propylaminosilane (DIPAS) with CN-1 Shower Head Type Reactor The silicon wafer was loaded into CN-1 PEALD reactor and heated to 300° C. with chamber pressure of 2 torr. DIPAS was delivered using bubbling method into the reactor. The ALD cycle was comprised of the process steps provided in Table 2 and using the following process parameters:

1. Introduce an organoaminosilane precursor to the reactor
   DIPAS: 50 sccm argon through the precursor container
   Argon flow: 100 sccm
   Si precursor pulse: 1 second
2. Inert gas purge
   Total flow of Argon and Nitrogen 500 sccm
   Purge time: 10 seconds
3. Plasma on
   Ar flow: 0 to 500 sccm
   Nitrogen flow: 0 to 500 sccm
   Total flow of Ar and nitrogen: 500 sccm
   Plasma power: 125 W (0.7 W/cm$^2$)
   Plasma time: 5 seconds
4. Plasma purge
   Total flow of Argon and Nitrogen: 500 sccm
   Purge time: 10 seconds Table 9 provides the process parameters and film properties of films deposited using DIPAS. Typical DIPAS films have carbon impurities of 1.2-2.2%.

TABLE 9

Process parameters and properties of silicon nitride containing films deposited using DIPAS

| Ar flow (sccm) | N$_2$ (sccm) | Ar/total flow (%) | GPC (Å/cycle) | % non-uniformity | Ref. Index | C content (% at) |
|---|---|---|---|---|---|---|
| 0 | 500 | 0 | 0.14 | 4.1 | 1.91 | 1.0 |
| 50 | 450 | 10 | 0.13 | 3.7 | 1.89 | N/A |
| 100 | 400 | 20 | 0.13 | 3.6 | 1.91 | 1.2 |
| 200 | 300 | 40 | 0.12 | 2.3 | 1.88 | N/A |
| 250 | 250 | 50 | 0.10 | 3.0 | 1.92 | 1.5 |
| 300 | 200 | 60 | 0.09 | 2.2 | 1.93 | N/A |
| 375 | 125 | 75 | 0.07 | 1.8 | 1.98 | 2.2 |
| 450 | 50 | 90 | 0.07 | 6.5 | 1.95 | N/A |
| 500 | 0 | 100 | 0.07 | 5.6 | 2.00 | 28.3 |

Example 10. PEALD Silicon and Nitrogen Containing Films Using Di-Iso-Propylaminosilane (DIPAS) in CN-1 Shower Head Type Reactor Silicon containing films were deposited from di-iso-propylaminosilane (DIPAS) and He/N$_2$ plasma. The process parameters and ALD steps were the same as described in Example 9, except that helium was used instead of Ar gas. Table 10 shows that films deposited using He/N$_2$ plasma and very low dilute HF wet etch resistance (WER). In all tested He/N$_2$ ratio, the film has WER>22.1 nm/min and refractive index lower than 1.85.

TABLE 10

Process parameters and film properties of silicon nitride containing films deposited from DIPAS and He/N$_2$ plasma

| He flow (sccm) | N$_2$ (sccm) | Ar/total flow | GPC (Å/cycle) | Ref. Index | dHF WER (nm/min) |
|---|---|---|---|---|---|
| 150 | 350 | 30% | 0.15 | 1.85 | >22.1 |
| 250 | 250 | 50% | 0.15 | 1.80 | >23.1 |
| 350 | 150 | 70% | 0.17 | 1.79 | >24.5 |

Example 11. PEALD Silicon Nitride Containing Films Using Di-Iso-Propylaminosilane (DIPAS) in CN-1 Shower Head Type Reactor

Si containing films were deposited from di-iso-propylaminosilane (DIPAS) and N$_2$ only plasma using screening PEALD reactor at 300° C. and chamber pressure of 2 torr with the following detail process parameters:

1. Introduce an organoaminosilane precursor to the reactor: DIPAS
   Delivery method: vapor draw
   Si precursor pulse: 1 second
   N$_2$ flow: 500 sccm
2. Inert gas purge
   N$_2$ flow: 500 sccm
   Purge time: 10 seconds
3. Plasma on
   Nitrogen flow: 500 sccm
   Plasma power: 125 W (0.7 W/cm$^2$)
   Plasma time: 5 seconds
4. Purge plasma
   Nitrogen flow: 500 sccm
   Purge time: 10 second

Growth per cycle is 0.15 Å/cycle with refractive index 1.93

The invention claimed is:

1. A plasma enhanced atomic layer deposition method of forming a silicon nitride film onto at least a surface of a substrate, the method comprising
   a. providing a substrate in a reactor;
   b. introducing into the reactor an at least one organoaminosilane represented by the following Formulas I, II and III below:

I

II $$\left( R^1 \diagdown \underset{|}{N} \diagdown R^2 \right)_n \\ \underset{|}{SiH_{3-n}} \\ SiH_3 \qquad \text{III}$$

wherein R¹ is selected from a linear or branched $C_3$ to $C_{10}$ alkyl group, a linear or branched $C_3$ to $C_{10}$ alkenyl group, a linear or branched $C_3$ to $C_{10}$ alkynyl group, a $C_1$ to $C_6$ dialkylamino group, an electron withdrawing group, and a $C_6$ to $C_{10}$ aryl group; R² is selected from hydrogen, a linear or branched $C_1$ to $C_{10}$ alkyl group, a linear or branched $C_3$ to $C_6$ alkenyl group, a linear or branched $C_3$ to $C_6$ alkynyl group, a $C_1$ to $C_6$ dialkylamino group, a $C_6$ to $C_{10}$ aryl group, an electron withdrawing group, and a $C_4$ to $C_{10}$ aryl group; optionally wherein R¹ and R² are linked together to form a ring selected from a substituted or unsubstituted aromatic ring or a substituted or unsubstituted aliphatic ring, and in Formula III n=1 or 2, wherein the at least one organoaminosilane reacts on at least a portion of the surface of the substrate to provide a chemisorbed layer;

c. purging the reactor with a purge gas;
d. introducing a plasma consisting essentially of nitrogen and noble gas into the reactor to react with at least a portion of the chemisorbed layer and provide at least one reactive site; and
e. purge the reactor with an inert gas; and wherein the steps b through e are repeated until a desired thickness of the silicon nitride film is obtained; wherein the silicon nitride film has a density of at least 2.7 g/cc.

2. The method of claim 1 wherein the at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, N-isopropylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, di-iso-propylaminodisilane, di-iso-butylaminodisilane, di-sec-butylaminodisilane, 2,6-dimethylpiperidinosilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane.

3. The method of claim 1 wherein the plasma comprises a noble gas selected from the group consisting of neon (Ne), argon (Ar), Xenon (Xe), krypton (Kr) and mixtures thereof.

4. The method of claim 1 wherein the method is conducted at one or more temperatures of about 400° C. or less.

5. The method of claim 1 wherein the method is conducted at one or more temperatures of about 300° C. or less.

6. A plasma enhanced atomic layer deposition method of forming a silicon nitride film onto at least a surface of a substrate, the method comprising the steps of:
a. providing a substrate in a reactor;
b. introducing into the reactor at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, N-isopropylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, di-iso-propylaminodisilane, di-iso-butylaminodisilane, di-sec-butylaminodisilane, 2,6-dimethylpiperidinosilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane wherein said introducing is for a period of 0.2 to 5 seconds and the at least one organoaminosilane reacts on at least a portion of the surface of the substrate;
c. purging the reactor with a purge gas comprising at least one selected from nitrogen, a noble gas, and combinations thereof;
d. introducing a nitrogen-noble gas containing plasma into the reactor; and
e. purge the reactor with an inert gas; and wherein the steps b through e are repeated until a desired thickness of the silicon nitride film is obtained wherein the nitride film has a refractive index of greater than 1.9 and a density of greater than 2.7 g/cc.

7. The method of claim 6 wherein the method is conducted at a temperature of 400° C. or less.

8. The method of claim 6 wherein the method is conducted at a temperature of 300° C. or less.

9. The method of claim 6 where the nitrogen-noble gas containing plasma consists essentially of a member selected from the group consisting of an argon/nitrogen plasma, a neon/nitrogen plasma, a krypton/nitrogen plasma, a xenon/nitrogen plasma, and combinations thereof.

10. A plasma enhanced atomic layer deposition method of forming a silicon nitride film onto at least a surface of a substrate, the method comprising the steps of:
a. providing a substrate in a reactor;
b. introducing into the reactor at least one organoaminosilane precursor is selected from the group consisting of di-iso-propylaminosilane, di-sec-butylaminosilane, phenylmethylaminosilane, 2,6-dimethylpiperidinosilane, N-methylcyclohexylaminosilane, N-ethylcyclohexylaminosilane, N-isopropylcyclohexylaminosilane, 2-methylpiperidinosilane, N-silyldecahydroquinoline, 2,2,6,6-tetramethylpiperidinosilane, 2-(N-silylmethylamino)pyridine, N-t-butyldisilazane, N-t-pentyldisilazane, N-(3-methyl-2-pyridyl)disilazane, N-(2-methylphenyl)disilazane, N-(2-ethylphenyl)disilazane, N-(2,4,6-trimethylphenyl)disilazane, N-(2,6-di-iso-pripylphenyl)disilazane, di-iso-propylaminodisilane, di-iso-butylaminodisilane, di-sec-butylaminodisilane, 2,6-dimethylpiperidinosilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, 1,1-(N,N'-di-tert-butylethylenediamino)disilane wherein the at least one organoaminosilane reacts on at least a portion of the surface of the substrate to provide a chemisorbed layer;

c. purging the reactor with a purge gas comprising at least one selected from nitrogen, a noble gas, and combinations thereof;
d. introducing a plasma comprising a noble gas into the reactor to react with at least a portion of the chemisorbed layer and provide an at least one reactive site wherein the plasma is generated at a power density ranging from about 0.01 to about 1.5 W/cm$^2$; and
e. purge the reactor with an inert gas; and wherein the steps b through e are repeated until a desired thickness of the silicon nitride film is obtained; wherein the silicon nitride film has a density of at least 2.7 g/cc.

11. The method of claim 10 wherein the method is conducted at a temperature of 400° C. or less.

12. The method of claim 10 wherein the noble gas plasma comprises a noble gas selected from the group consisting of neon (Ne), argon (Ar), Xenon (Xe), krypton (Kr) and mixtures thereof.

13. A plasma enhanced atomic layer deposition method of forming a silicon nitride film onto at least a surface of a substrate, the method comprising
    a. providing a substrate in a reactor;
    b. introducing into the reactor an at least one organoaminosilane represented by the following Formula below:

wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring, and n=1 or 2;
    c. purging the reactor with a purge gas;
    d. introducing a plasma consisting essentially of nitrogen into the reactor; and
    e. purge the reactor with an inert gas; and wherein the steps b through e are repeated until a desired thickness of the silicon nitride film is obtained; and wherein the silicon nitride film has a refractive index of greater than 1.9 and a density of greater than 2.7 g/cc.

14. The method of claim 13 wherein the organoaminosilane comprises at least one member selected from the group consisting of di-iso-propylaminodisilane, di-iso-butylaminodisilane, di-sec-butylaminodisilane, 2,6-dimethylpiperidinosilane, N-methylcyclohexylaminodisilane, N-ethylcyclohexylaminodisilane, phenylmethylaminodisilane, 2-(N-disilylmethylamino)pyridine, N-phenylethyldisilane, N-isopropylcyclohexylaminodisilane, and 1,1-(N,N'-di-tert-butylethylenediamino)disilane; and the plasma further consists essentially of a argon.

15. A plasma enhanced atomic layer deposition method of forming a silicon nitride film onto at least a surface of a substrate, the method comprising
    a. providing a substrate in a reactor;
    b. introducing into the reactor for a period of about 0.001 to about 500 seconds at least one organoaminosilane represented by the following Formula I below:

wherein R$^1$ is selected from a linear or branched C$_3$ to C$_{10}$ alkyl group, a linear or branched C$_3$ to C$_{10}$ alkenyl group, a linear or branched C$_3$ to C$_{10}$ alkynyl group, a C$_1$ to C$_6$ dialkylamino group, an electron withdrawing group, and a C$_6$ to C$_{10}$ aryl group; R$^2$ is selected from hydrogen, a linear or branched C$_1$ to C$_{10}$ alkyl group, a linear or branched C$_3$ to C$_6$ alkenyl group, a linear or branched C$_3$ to C$_6$ alkynyl group, a C$_1$ to C$_6$ dialkylamino group, a C$_6$ to C$_{10}$ aryl group, an electron withdrawing group, and a C$_4$ to C$_{10}$ aryl group; optionally wherein R$^1$ and R$^2$ are linked together to form a ring selected from a substituted or unsubstituted aromatic ring or a substituted or unsubstituted aliphatic ring;
    c. purging the reactor with a purge gas;
    d. introducing a plasma consisting essentially of nitrogen and noble gas into the reactor for a period of about 0.1 to about 100 seconds; and
    e. purge the reactor with an inert gas; and wherein the steps b through e are repeated until a desired thickness of the silicon nitride film is obtained; wherein the silicon nitride film has a density of at least 2.7 g/cc.

* * * * *